United States Patent
LeBlanc (10) Patent No.: US 10,234,273 B1
(45) Date of Patent: *Mar. 19, 2019

(54) SYSTEM AND METHOD FOR PHOTOGRAPHIC INSPECTION AND DOCUMENTATION OF POST-TENSIONED CONCRETE TENDON TERMINATIONS

(71) Applicant: Mark LeBlanc, Boynton Beach, FL (US)

(72) Inventor: Mark LeBlanc, Boynton Beach, FL (US)

(\*) Notice: Subject to any disclaimer, the term of this patent is extended or adjusted under 35 U.S.C. 154(b) by 0 days.

This patent is subject to a terminal disclaimer.

(21) Appl. No.: 15/590,366

(22) Filed: May 9, 2017

Related U.S. Application Data (63) Continuation of application No. 14/795,428, filed on Jul. 9, 2015, now Pat. No. 9,644,946.

(51) Int. Cl.
| | | |
|---|---|---|
| *G01N 21/00* | (2006.01) | |
| *G01B 11/04* | (2006.01) | |
| *E04C 5/08* | (2006.01) | |

(52) U.S. Cl.
CPC .............. *G01B 11/043* (2013.01); *E04C 5/08* (2013.01); *G01N 21/00* (2013.01)

(58) Field of Classification Search
CPC .. G01B 11/04; G01B 3/04; E04C 5/08; G01N 21/64; G01N 21/68; H01J 37/32935; G01J 3/02
See application file for complete search history.

(56) References Cited

U.S. PATENT DOCUMENTS

| | | | |
|---|---|---|---|
| 5,065,249 A | | 11/1991 | Horn et al. |
| 5,142,793 A | * | 9/1992 | Crane .................. G01B 3/1061 33/755 |
| 6,056,450 A | * | 5/2000 | Walling ................ F16M 11/10 352/243 |
| 6,538,732 B1 | | 3/2003 | Drost et al. |
| 6,773,525 B2 | | 8/2004 | Shinohara et al. |
| 6,907,799 B2 | | 6/2005 | Jacobsen et al. |
| 6,923,542 B2 | | 8/2005 | Harris |
| 7,931,412 B2 | | 4/2011 | Brown |
| 8,002,480 B2 | | 8/2011 | Polster |
| 8,054,459 B2 | | 11/2011 | Lindner |
| 8,169,477 B2 | | 5/2012 | Tawfiq |
| 8,640,558 B2 | | 2/2014 | Cabuz |
| 8,830,391 B2 | | 9/2014 | Scarola |
| 9,644,946 B1 | * | 5/2017 | LeBlanc .............. G01B 11/043 |
| 2008/0145046 A1 | | 6/2008 | Ho |

\* cited by examiner

*Primary Examiner* — Abdullahi Nur
(74) *Attorney, Agent, or Firm* — Mark D. Bowen; Malin Haley DiMaggio & Bowen, P.A.

(57) ABSTRACT

An image-capture inspection and documentation system is provided to capture images of post-tensioned concrete anchorage structures to verify and document proper tendon terminations in post-tensioned concrete structures. A method is disclosed for using such an image-capture inspection system to inspect, verify, and document the tendon tail-end terminations within recessed grout pockets for multiple anchorage locations while generating a digital image of each location with visual indications for both tendon tail-end termination and anchorage location identification for each such location.

6 Claims, 7 Drawing Sheets

SYSTEM AND METHOD FOR PHOTOGRAPHIC INSPECTION AND DOCUMENTATION OF POST-TENSIONED CONCRETE TENDON TERMINATIONS

CROSS REFERENCE TO RELATED APPLICATIONS

This application is a continuation of U.S. patent application Ser. No. 14/795,428, filed on Jul. 9, 2015.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all rights whatsoever.

BACKGROUND OF THE INVENTION

1 Field of the Invention

The present invention relates generally to post-tensioned concrete structures, and more particularly to a system and method for inspection and documentation of tendon terminations in post-tensioned concrete structures.

2. Description of Related Art

Concrete is a well-known construction material that has been in use in the construction of concrete structures for thousands of years. Post-tensioning is a type of steel reinforcement for concrete structures. Compressive forces are induced in a concrete structure by tensioning steel tendons comprised of strands or bars placed in ducts embedded in the concrete. The tendons are installed after the concrete has been placed and sufficiently cured to a prescribed initial compressive strength. A hydraulic jack is attached to one or both ends of the tendon and pressurized to a predetermined value while bearing against the end of the concrete structure. This induces a predetermined force in the tendon and the tendon elongates elastically under this force. After jacking to the full required force, the tendon is transferred from the jack to an end anchorage.

Tendons made up of strands are secured by steel wedges that grip each strand and seat firmly in a wedge plate disposed within a recess, known as a grout pocket. The wedge plate itself carries all the strands and bears on a steel anchorage. The anchorage may be a simple steel bearing plate or may be a special casting with two or three concentric bearing surfaces that transfer the tendon force to the concrete. The protruding "tails" or strands or bars of permanent tendons are cut off using an abrasive disc saw or plasma cutter after stressing. Tendons are then grouted using a cementitious based grout which fills the grout pocket.

Post tension tendons are protected from corrosion along most of the lengths thereof by a coating of grout, grease, and/or a plastic sheath depending on the application. The bare anchorage and terminal ends of the tendons, however, are typically protected by installation of grease and a grease cap, and the grout pocket is further sealed by concrete grout. If the tendon ends are not adequately protected, significant corrosion problems can arise. Typically, the end of the tendon must be cut off a specified distance from the recessed anchorage assembly to allow for sufficient grout coverage to prevent corrosion-inducing moisture penetration. The tail-ends of the tendons are typically required to extend within the grout pocket a specified distance (e.g. 0.5", 0.75" or 1.25") beyond the anchorage per code and/or industry specification.

In order to verify that the concrete structure has been built to proper specification, construction personnel are often required to verify and document that the tendons have been terminated at the specified length. This process has proven difficult, time consuming, and hazardous, particularly with multistory structures, as the grout pockets are typically formed on the exterior of the structure and inspection will typically occur before walls are erected. As should be apparent, obtaining visual confirmation of tendon terminations recessed within grout pockets formed on the exterior surfaces of partially constructed concrete buildings presents numerous challenges and hazards.

Accordingly, there exists a need for an apparatus and method for inspecting, verifying, and documenting tendon terminations in post-tensioned concrete structures.

BRIEF SUMMARY OF THE INVENTION

The present invention overcomes the limitations and disadvantages present in the art by providing an apparatus and method for inspecting and documenting tendon anchorage structures in post-tensioned concrete structures to ensure that a tendon terminates a sufficient distance beyond its anchorage in accordance with design specifications. In accordance with a first aspect of the present invention, an image-capture inspection and documentation apparatus is provided to capture images of post-tensioned concrete anchorage structures which verifies and documents the proper tendon terminations in post-tensioned concrete structures. In accordance with a second aspect of the present invention, a method is disclosed for using such an image-capture inspection system to inspect, verify, and document the tendon tail-end terminations within recessed grout pockets for multiple anchorage locations while generating a digital image of each location with visual indications for both tendon tail-end termination and anchorage location identification for each such location.

An apparatus according to the present invention comprises an operator supported remote imaging system including an elongate support pole or boom having a camera platform mounted at the top end thereof. A digital imaging device and a light unit are mounted to the platform and oriented so capture images of post-tensioned tendon terminations when property positioned by the operator. A linear measuring device, marked with length measuring indicia (e.g. inches, centimeters, or bold marking indicia etc.) projects from a front end of the platform within the field of view of the video camera and functions to provide a visual indication of the distance which the tail-end of a tendon projects from the recessed anchorage. A manually adjustable alpha-numeric location code device is also mounted to the platform within the filed of view of the camera and allows the operator to set alpha and/or numeric indicia to correspond to the location being inspected.

A method for using such a video inspection system to inspect, verify, and document the tendon terminations for multiple anchorage locations using an apparatus of the present invention involves: (a) identifying on construction plans a plurality of post-tensioned cable anchorage assemblies formed within a recessed grout pockets for inspection, each anchorage assembly identified by a location code; (b) identifying the physical location of one of said anchorage assemblies; (c) setting the location code for said anchorage assembly on the location code device; (d) activating the light device; (e) placing the camera platform in proximity to the grout pocket such that the projecting linear measuring device extends fully into the recess; (f) capturing an image of at least portions of the anchorage assembly, the linear measuring device, and the location code displayed on the location code device; and (g) repeating the process for various other anchorage locations. The digital image may be captured directly by the digital camera device or may be captured on a remote tablet computer via Bluetooth or Wi-Fi wireless transmission.

In accordance with these and other objects, which will become apparent hereinafter, the instant invention will now be described with particular reference to the accompanying drawings.

DETAILED DESCRIPTION OF THE INVENTION

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawings, FIGS. 1-7 illustrate an apparatus, generally referenced as 10, and method for using said apparatus to inspect and document tendon tail-end terminations within recessed grout pockets post-tensioned concrete structures to ensure that the tendons have been terminated a specified distance from the anchorage assembly.

In accordance with a first aspect of the present invention, a camera inspection and documentation apparatus 10 is provided to capture images of post-tensioned concrete anchorage structures which verify and document the recessed depth of the anchorage and tendon terminations. Apparatus 10 comprises an operator supported remote video inspection system including an elongate support pole or boom 12 having a camera platform 14 mounted to the top end portion of pole 12. In various contemplated embodiments, camera platform 14 may be fixedly mounted or removably mounted to pole 12. Further, platform 14 may be mounted to a lower end portion of pole 12 so as to allow the operator to lower the platform for inspection applications in non-elevated positions. Pole 12 preferably comprises an elongate, lightweight rigid member having a length of approximately between 3.0-6.0 feet, however any suitable length is considered within scope of the present invention. Further, pole 12 may comprise a one-piece structure or may comprise a telescopically adjustable multi-piece assembly. Pole 12 functions to allow the operator to position the camera platform relative to elevated recessed grout pockets formed in post-tensioned concrete structures. It will also become apparent that apparatus 10 may be used without pole 12 in situations wherein grout pockets are not elevated and/or otherwise readily accessible. It is further contemplated that platform 14 may be affixed to a lower end of pole 12 such that the system may be employed to inspect tendon terminations within grout pockets that are disposed below the surface upon which the operator is standing.

A digital camera 16 and light unit 18 are mounted to the camera platform. Camera 16 is preferably a small, lightweight digital video camera, such as a GOPRO®, or any other suitable video camera. GOPRO® is a registered trademark of GoPro, Inc. In a contemplated alternate embodiment, a digital still camera may be used in place of a video camera. Camera 16 is a fully functional self-contained, battery powered unit that preferably receives a data storage SD memory card for storing digital imagery. Camera 16 is further preferably adapted to wirelessly transmit images via Wi-Fi or other suitable wireless communication protocol, such as BLUE TOOTH In accordance with this aspect, pole 12 may be adapted to include a camera triggering device to allow the user to selective activate camera 16. Accordingly, as used herein the term "camera" shall broadly be construed to mean any suitable video or still digital or non-digital (e.g. film) image capture device. Light unit 18 is preferably a self-contained, battery powered illumination device, such as an LED lamp, flashlight, or other illumination device. Camera 16 and light unit 18 are preferably mounted to platform 14 in a forward facing direction and oriented so capture images post-tensioned anchorages when property positioned by the operator. In a preferred embodiment, camera 16 is mounted in an elevated position relative to light unit 18, however, any suitable mounting configuration is considered within the scope of the present invention. In addition, camera 16 and light unit 18 may be integrally formed as a single camera unit, i.e. light unit 16 may comprise the camera flash.

Platform 14 includes a front portion from which a linear measuring device 20 projects terminating at a distal end. Linear measuring device 20 preferably comprises a ruler-type measuring device marked with length measuring indicia, such as English units (e.g. inches), metric units (e.g. centimeters) or other suitable measuring markings or indicia. The length measuring indicia preferably originate with "zero" disposed at the distal end 21, and increase in regular increments from the distal end toward platform 14. As noted above, linear measuring device 20 projects from a front end of platform 14. It is important that measuring device 20 project within the field of view of digital camera 16 such that the measuring indicia are within the field of view and thus appear in captured images to provide a visual indication of the terminal end of the tendon relative to measuring device 20. Measuring device 20 preferably may further be adapted with bold marking, tape, or other adjustable bold marker 23 disposed at a predetermined specified distance from distal end 21, which specified distance corresponds to a maximum distance at which the tendon may extend from its anchorage assembly. Providing a bold marker 23 on measuring device 20 allows for easily identifiable confirmation that the tail-end of the tendon has been trimmed so as to be sufficiently recessed from the face of the structure within the grout pocket.

A manually adjustable alpha-numeric location code device 22 is also mounted to platform 14 within the field of view of the camera 16 so as to present a visual location identification code within captured images. Location code device 22 preferably comprises a device having a plurality of rotatably adjustable wheels 25, with each wheel having a plurality of alpha-numeric indicia, including numerical indicia (e.g. 0-9) and/or alphabetical indicia (e.g. A, B, C, etc.) disposed thereon, whereby code device 22 may be manually set to a display corresponding to an anchorage location corresponding to the location being inspected as set forth on the plans/blueprints (e.g. 189A, 189B, etc.). Since each tendon anchorage location within a post-tensioned concrete structure is identified on the blueprints or plans by a location code, location code device 22 is preferably adapted such that the location code may be adjusted for each such location to correspond to the location identified on the plans. As noted above, it is important that both the measuring device 20 and code device 22 be mounted so as to appear within the field of view a digital camera 16. This configuration allows a single photographic image to capture both the tendon tail-end termination relative to measuring device 20, as well as the location code displayed on the alpha-numeric location code device 22 thereby providing visual confirmation and documentation that the tendon has been properly terminated (e.g. trimmed) a proper distance from the anchorage assembly within the grout pocket. Location code device 22 may comprise a manually adjustable mechanical device or an adjustable electronic device capable of displaying any suitable location code or location identifying phrase or description (e.g. $2^{nd}$ Floor NE 0001A).

In a first configuration, digital camera 16 is mounted in an elevated position relative to light unit 18, linear measuring device 20, and location code device 22. In this configuration, light unit 18 is able to shine directly into the grout pocket while camera 16 has both the linear measuring device 20, as well as location code device 22 within its field of view. It should be noted, however, that alternate equivalent mounting configurations may be used without departing from the essential aspects of the invention. More particularly, provided that the linear measuring device 20 and location code device 22 are visible to digital camera 16, virtually any mounting configuration may be employed.

In accordance with a second aspect of the present invention, a method is disclosed for inspecting and documenting the spacing between the anchorage assembly and the terminal end of the tendon for multiple anchorage locations using the camera inspection system disclosed herein. In a preferred embodiment, the method includes the steps of:

(a) identifying on construction plans a plurality of post-tensioned cable anchorage assemblies formed within a recessed grout pockets for inspection, each anchorage assembly identified by a location code;

(b) identifying the physical location of one of said anchorage assemblies;

(c) setting the location code for said anchorage assembly on the location code device (22);

(d) activating the light device (18);

(e) placing the camera platform 14 in proximity to the grout pocket such that the projecting linear measuring device 20 extends fully into the recess;

(f) obtaining an imagery of at least portions of the anchorage assembly, the linear measuring device, and the location code displayed on the location code device;

(g) wirelessly transmitting the imagery to a remote tablet computer;

(h) capturing an image on the tablet computer from the wirelessly transmitted imagery; and (i) repeating the process for various other anchorage locations.

In an alternate method, video data may then be captured and stored on the camera and later processed to extract still images for each such anchorage assembly, with each still image depicting the location code and recess depth for the anchorage structure.

Figure 1:
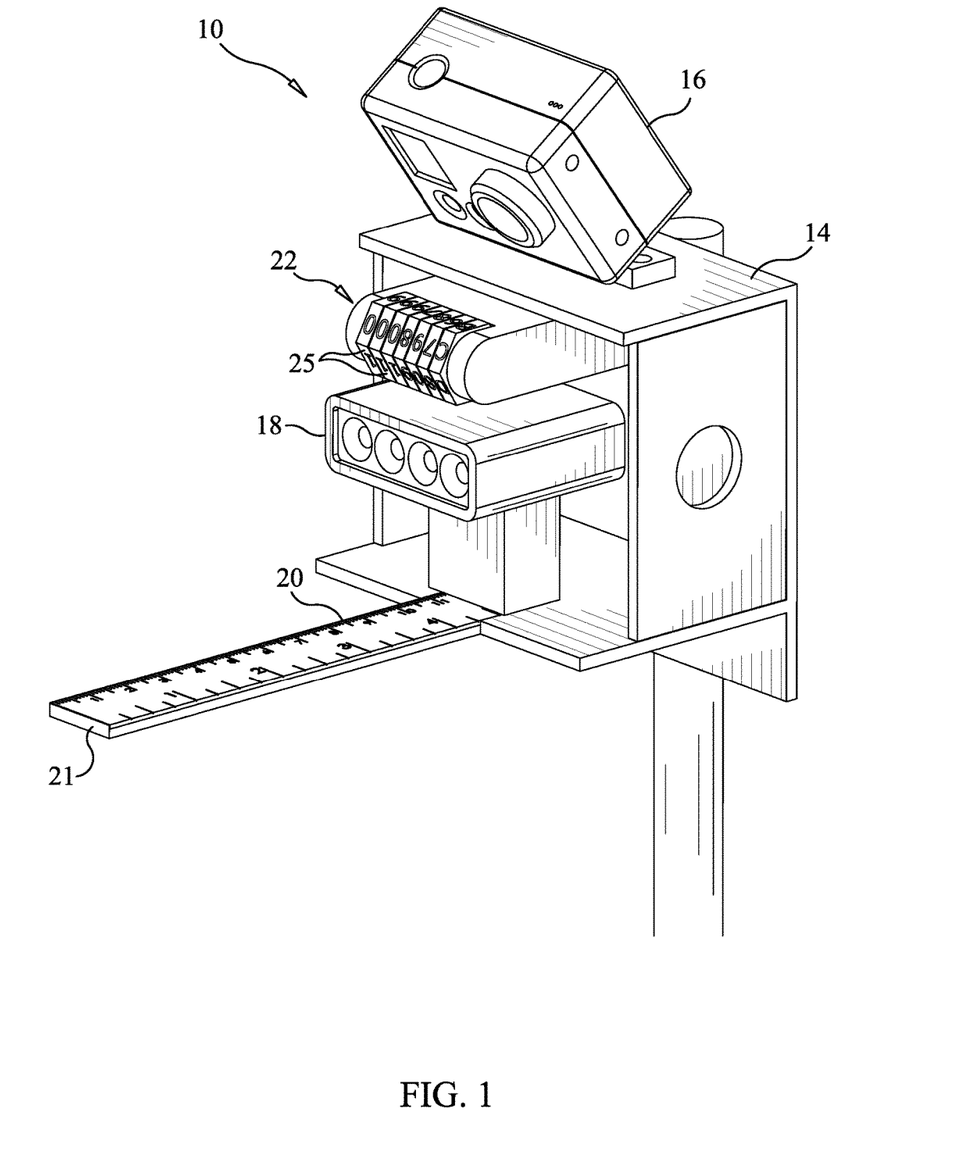
FIG. 1 is a front perspective view of an apparatus for inspecting and documenting tendon terminations in post-tensioned concrete structures in accordance with the present invention.
Figure 2:
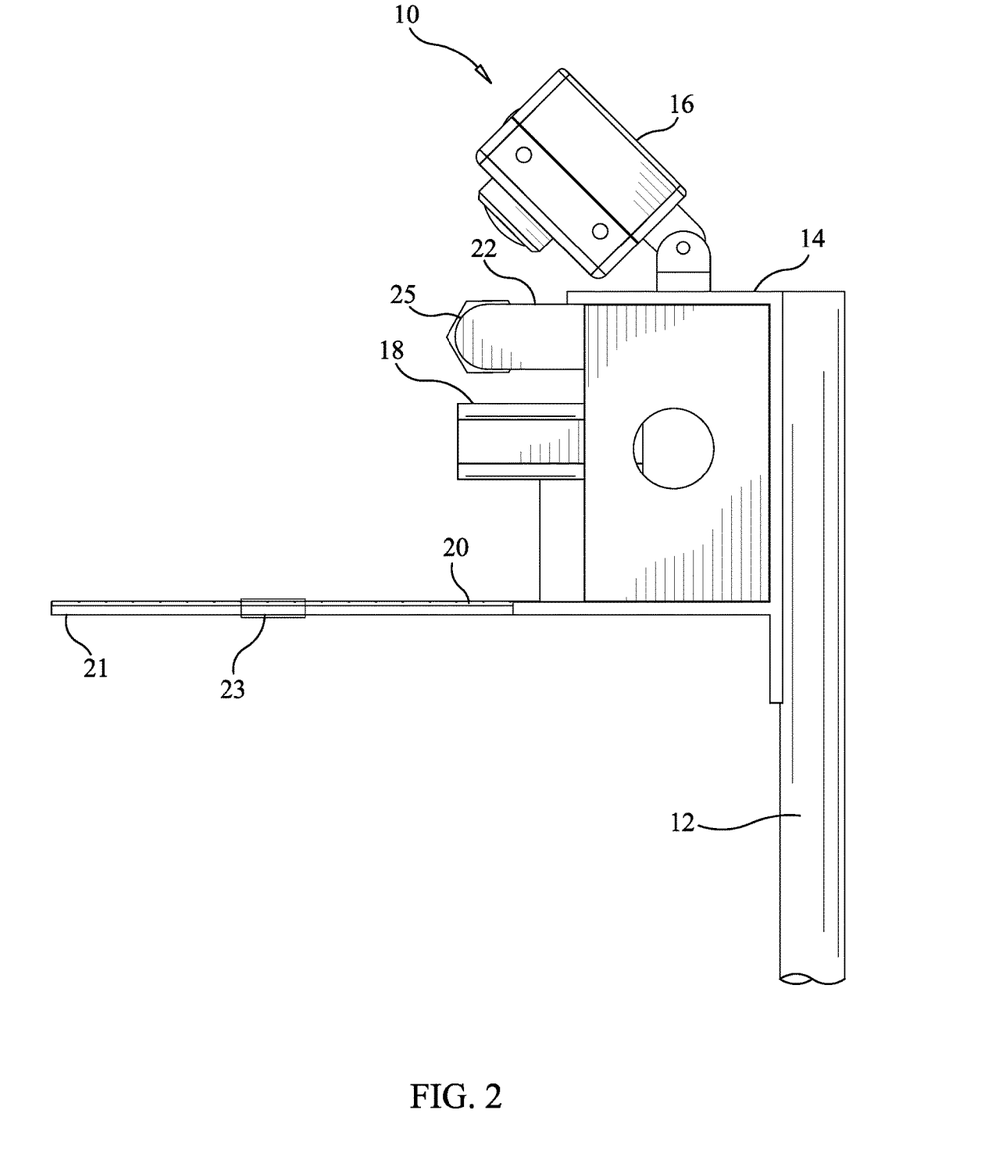
FIG. 2 is a side view thereof.
Figure 3:
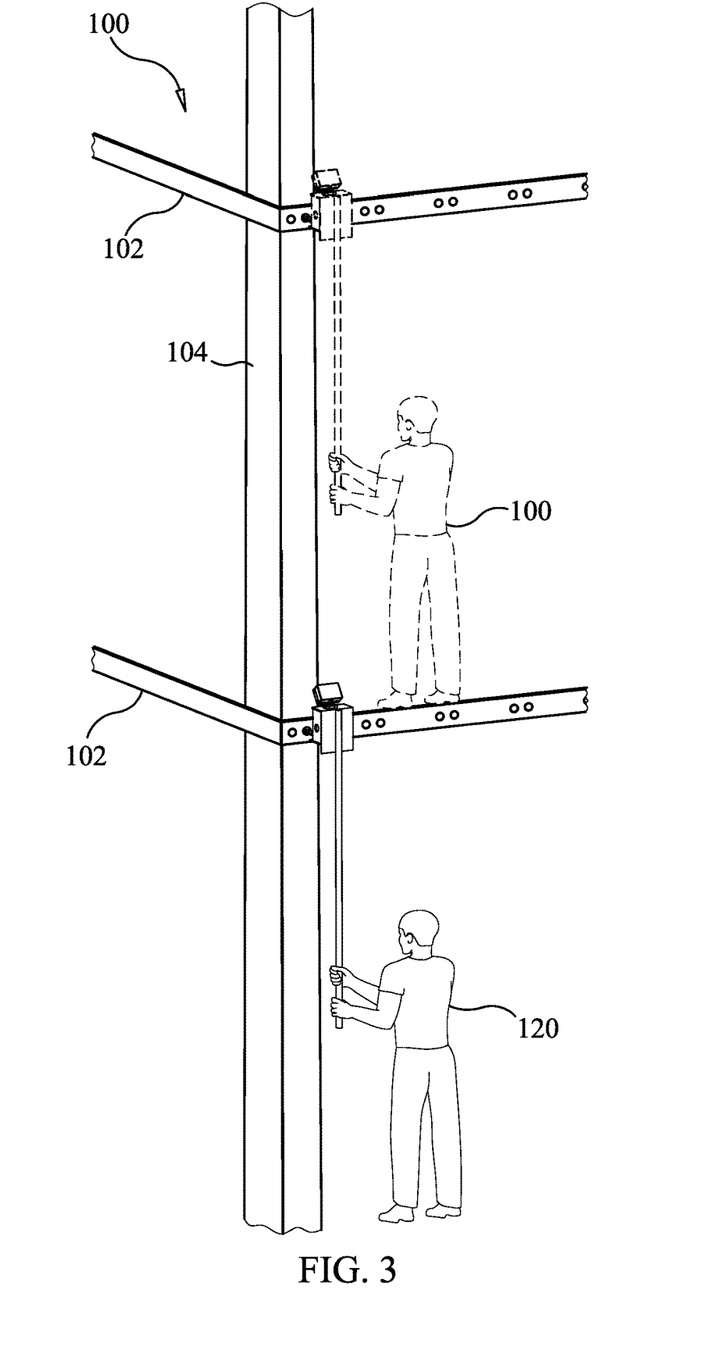
FIG. 3 illustrates use of the tendon termination inspection apparatus on a multi-level concrete structure.
Figure 4:
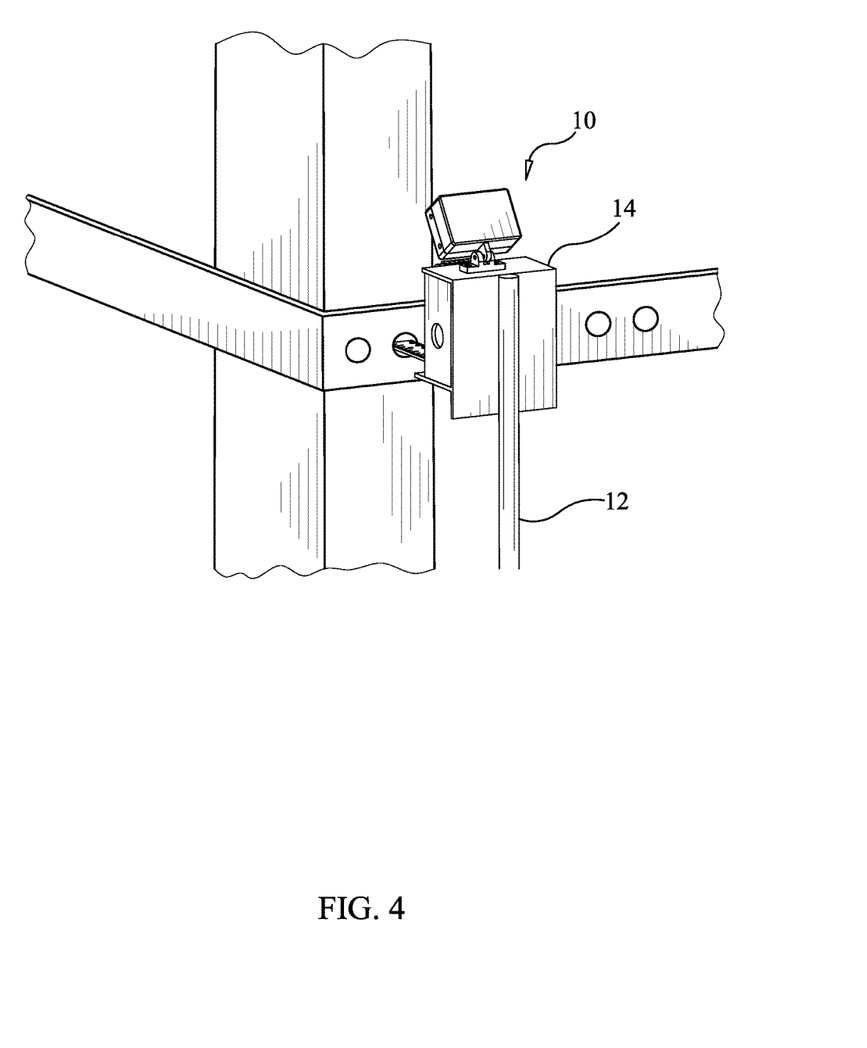
FIG. 4 is a partial detail rear perspective view of the tendon termination inspection apparatus disposed in an operative position for conducting an inspection.
Figure 5:
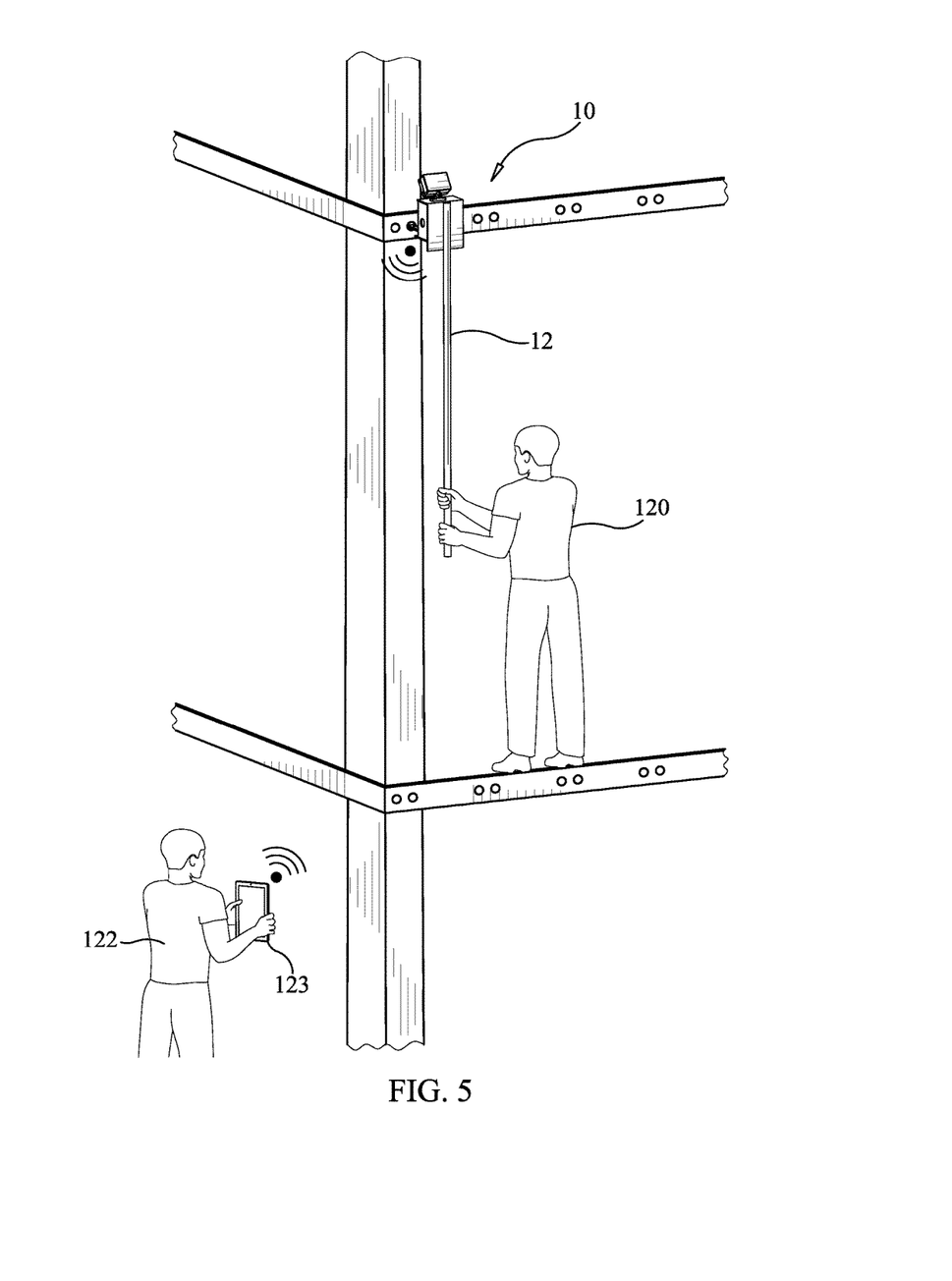
FIG. 5 is a perspective illustration showing the tendon termination inspection device in use.
Figure 6:
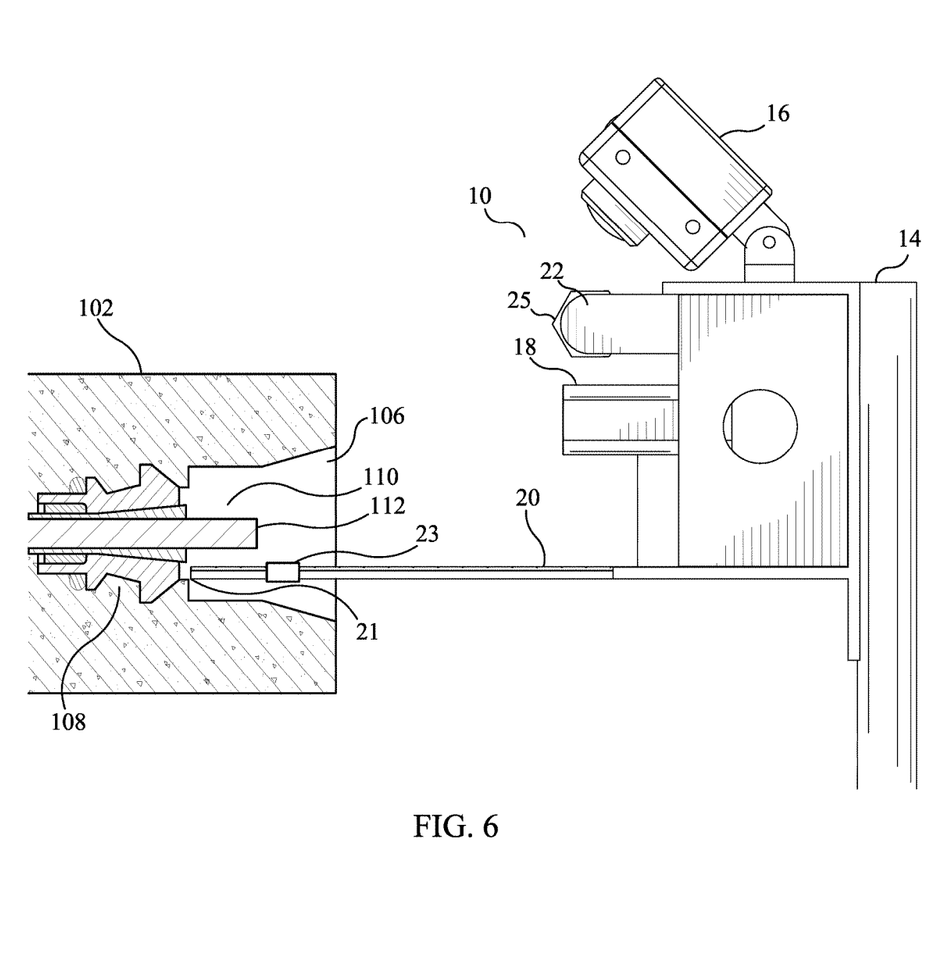
FIG. 6 is a side view illustration showing the tendon termination inspection apparatus deployed in an inspection mode relative to a tendon anchorage assembly within a recessed grout pocket of a post-tensioned concrete slab depicted in sectional view.
Figure 7:
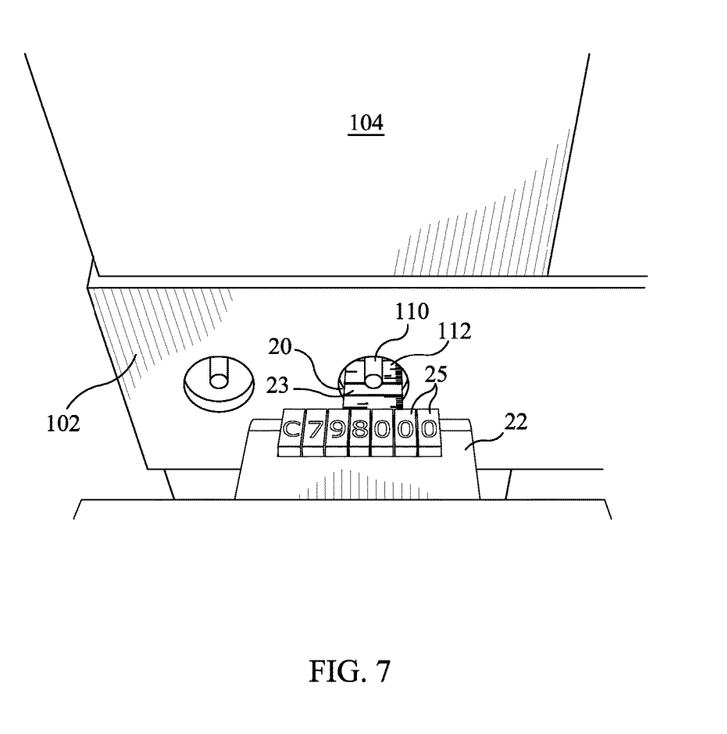
FIG. 7 is an illustration of a photographic image captured by the apparatus documenting the termination spacing of the tendon tail end from the anchorage assembly.

FIGS. 3-7 illustrate the use of inspection system 10 to inspect and document tendon terminations associated with anchorage assemblies disposed within recessed grout pockets formed in post-tensioned concrete structures. More particularly, a concrete structure 100 is formed having post-tensioned concrete slabs, referenced as 102, supported in spaced relation by columns 104. Each concrete slab 102 includes an edge defining a plurality of recessed grout pockets, referenced as 106. As best illustrated in FIG. 6, each grout pocket 106 contains an anchorage assembly, generally referenced as 108, which secures a cable or tendon 110. Tendon 110 includes a tail end portion 112 that extends beyond anchorage assembly within the grout pocket. Inspection system 10 is maneuvered into position by a user 120 such that measuring device 20 fully extends into the grout pocket as illustrated in FIG. 6. As should now be apparent, pole 12 is useful in allowing user 120 to properly position inspection system 10 within elevated grout pockets formed in overhead slabs, as well as grout pockets formed in structures below where the operator is standing. FIG. 6 illustrates inspection system 10 positioned within a grout pocket 106 with the distal end 21 of measuring device 20 in abutment with the anchorage assembly 108 whereby the extending tail end of tendon 110 extends over the top/marked surface of measuring device 20. FIG. 7 illustrates a view captured by camera 16, and in particular within the captured image is the location code as displayed by code device 22 as well as an image confirming that the tail end 112 of tendon 110 terminates a specified distance from the anchorage assembly which may be visually confirmed by the position of the tail end relative to marking 23 on measuring device 20. The image is preferably wirelessly transmitted from camera 16 to a tablet computer 123 operated by an assistant 122 as illustrated in FIG. 5.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A system for inspecting tendon terminations disposed within recessed grout pockets formed in post-tension concrete structures, said system comprising:
    an inspection assembly including a camera, a light device, and a linear measuring device;
    said camera adapted to capture images within a field of view located in front of said inspection assembly;
    said light device disposed so as to project light within said field of view; and
    said linear measuring device projecting within said field of view.

2. The system according to claim 1, further including a pole attached to said inspection assembly.

3. The system according to claim 1, further including a location code device being operator adjustable to display a predetermined location code, said location code being displayed within the field of view of said camera.

4. A method for inspecting tendon terminations disposed within recessed grout pockets formed in post-tension concrete structures, said method including the steps of:
    (a) providing an inspection assembly comprising a camera adapted to capture images within a field of view located in front of said inspection assembly, a light device disposed so as to project light within said field of view, and a linear measuring device projecting within said field of view;
    (b) placing said inspection assembly in proximity to the grout pocket such that said linear measuring device extends fully into the grout pocket recess;
    (f) activating said camera and said light device to obtain an image depicting the tendon termination in proximity to said linear measuring device.

5. The method according to claim 4, further including the step of wirelessly transmitting said image to a remote tablet computer.

6. The method according to claim 4 including providing said inspection assembly with a location code device being operator adjustable to display a predetermined location code, said location code being displayed within the field of view of said camera.

* * * * *